United States Patent [19]

Chu

[11] Patent Number: 4,590,323

[45] Date of Patent: May 20, 1986

[54] CONVERSION OF PARAFFINS TO AROMATICS OVER ZEOLITES MODIFIED WITH OXIDES OF GROUP IIIA, IVA AND VA ELEMENTS

[75] Inventor: Chin-Chiun Chu, North Brunswick, N.J.

[73] Assignee: Mobil Oil Corporation, New York, N.Y.

[21] Appl. No.: 744,086

[22] Filed: Jun. 12, 1985

[51] Int. Cl.$^4$ ................................................. C07C 2/00
[52] U.S. Cl. .................................... 585/417; 585/407; 585/415
[58] Field of Search ...................... 585/407, 415, 417

[56] References Cited

U.S. PATENT DOCUMENTS

| | | | |
|---|---|---|---|
| 2,329,672 | 9/1943 | Weizmann | 585/417 |
| 3,374,281 | 3/1968 | Csicsery | 585/417 |
| 3,760,024 | 9/1973 | Cattanach | 585/417 |
| 3,928,174 | 12/1975 | Bonacci et al. | 585/475 |
| 3,945,913 | 3/1976 | Brennan et al. | 585/473 |
| 4,078,990 | 3/1978 | Brennan et al. | 585/475 |
| 4,120,910 | 10/1978 | Chu | 585/417 |
| 4,175,057 | 11/1979 | Davies et al. | 502/61 |
| 4,197,214 | 4/1980 | Chen et al. | 585/407 |
| 4,302,620 | 11/1981 | Chu | 585/467 |
| 4,302,621 | 11/1981 | Chu | 585/467 |
| 4,302,622 | 11/1981 | Chu | 585/467 |
| 4,341,622 | 7/1982 | Tabak et al. | 502/42 |
| 4,350,835 | 9/1982 | Chester et al. | 585/415 |
| 4,458,097 | 7/1984 | Garska et al. | 585/415 |
| 4,469,909 | 9/1984 | Chester et al. | 585/481 |

*Primary Examiner*—John Doll
*Assistant Examiner*—A. Pal
*Attorney, Agent, or Firm*—Alexander J. McKillop; Michael G. Gilman; Edward F. Kenehan, Jr.

[57] ABSTRACT

There is provided a process for producing aromatic hydrocarbons from paraffins. The process involves contacting one or more $C_2$–$C_{12}$ alkanes with a catalyst containing a zeolite, such as ZSM-5, modified with one or more oxides of Group IIIA, IVA or VA elements, such as Sc, Ti or V. The presence of these particular oxide modifiers has been observed to result in greater yields of aromatics including BTX.

13 Claims, No Drawings

CONVERSION OF PARAFFINS TO AROMATICS OVER ZEOLITES MODIFIED WITH OXIDES OF GROUP IIIA, IVA AND VA ELEMENTS

BACKGROUND

The present invention relates to a process for producing aromatics from alkanes with a catalyst comprising a zeolite such as ZSM-5 modified with one or more oxides of Group IIIA, IVA and VA elements.

The Chester et al U.S. Pat. No. 4,350,835 describes a process for converting ethane to liquid aromatics by contacting the ethane with a zeolite catalyst such as ZSM-5 having incorporated therein a minor amount of gallium The Davies et al U.S Pat. No. 4,175,057 describes a process for producing aromatics by contacting a $C_3$-$C_8$ hydrocarbon with a gallium catalyst supported on an aluminosilicate in which the ratio of silica to alumina is between 20:1 and 70:1.

U.S. Pat. No. 4,120,910 to Pochen Chu describes a process for converting ethane to aromatics with a zeolite catalyst such as ZSM-5 having incorporated therein a metal selected from Groups VIII, IIB and IB of the Periodic Table. Examples of such metals include copper, zinc, ruthenium, rhodium, palladium, platinum, iridium and osmium U.S. Pat. Nos. 4,302,620, 4,302,621 and 4,302,622, all to Chin-Chiun Chu, describe the conversion of aromatic compounds to dialkylbenzene compounds with catalysts comprising a zeolite such as ZSM-5 modified with an oxide of Group IVA, VA and IIIA elements, respectively Examples of such Group IVA elements include Ti, Zr and Hf; examples of such Group VA elements include V, Nb and Ta; and examples of such Group IIIA elements include Sc, Y and Sm.

The entire disclosures of the above-mentioned U.S. Patents are expressly incorporated herein by reference.

SUMMARY

According to one aspect of the present invention, there is provided a process for producing aromatic hydrocarbons, said process comprising contacting one or more $C_2$-$C_{12}$ alkanes with a catalyst comprising a crystalline zeolite material having a constraint index within the approximate range of 1 to 12, said contacting taking place under sufficient aromatization conditions, said catalyst further comprising an oxide of a Group IIIA, IVA or VA element.

EMBODIMENTS

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen atoms is 1:2. The electrovalence of the tetrahedra containing aluminum is balanced by the inclusion in the crystal of a cation, for example an alkali metal or an alkaline earth metal cation. This can be expressed wherein the ratio of aluminum to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given aluminosilicate by suitable selection of the cation. The spaces between the tetrahedra are occupied by molecules of water prior to dehydration.

Although zeolites may contain silica and alumina, it is recognized that the silica and alumina portions may be replaced in whole or in part with other oxides More particularly, $GeO_2$ is an art recognized substitute for $SiO_2$ and $B_2O_3$, $Cr_2O_3$, $Fe_2O_3$, and $Ga_2O_3$ are art recognized replacements for $Al_2O_3$. Accordingly, the term zeolite as used herein shall connote not only materials containing silicon and, optionally, aluminum atoms in the crystalline lattice structure thereof, but also materials which contain suitable replacement atoms for such silicon and/or aluminum. On the other hand, the term aluminosilicate zeolite as used herein shall define zeolite materials consisting essentially of silicon and, optionally, aluminum atoms in the crystalline lattice structure thereof, as opposed to materials which contain substantial amounts of suitable replacement atoms for such silicon and/or aluminum.

An important characteristic of the crystal structure of the particular class of zeolites suitable for use in accordance with the present invention is that it provides a selective constrained access to and egress from the intracrystalline free space by virtue of having an effective pore size intermediate between the small pore Linde A and the large pore Linde X, i.e. the pore windows of the structure are of about a size such as would be provided by 10-membered rings of silicon atoms interconnected by oxygen atoms. It is to be understood, of course, that these rings are those formed by the regular disposition of the tetrahedra making up the anionic framework of the crystalline zeolite, the oxygen atoms themselves of the aluminosilicate zeolites being bonded to the silicon or aluminum atoms at the centers of the tetrahedra. Briefly, the preferred type of aluminosilicate zeolites useful in this invention possess, in combination: a silica to alumina mole ratio of at least about 12; and a structure providing constrained access to the intracrystalline free space.

The silica to alumina mole ratio referred to may be determined by conventional analysis. This ratio is meant to represent, as closely as possible, the ratio in the rigid anionic framework of the zeolite crystal and to exclude aluminum in the binder or in cationic or other form within the channels. Although aluminosilicate zeolites with a silica to alumina mole ratio of at least 12 are useful, it is preferred in some instances to use aluminosilicate zeolites having substantially higher silica/alumina ratios, e.g. 70 and above, 200 and above or even 1600 and above. In addition, aluminosilicate zeolites as otherwise characterized herein but which are substantially free of aluminum, that is zeolites having silica to alumina mole ratios of up to infinity, are found to be useful and even preferable in some instances. Such "high silica" or "highly siliceous" aluminosilicate zeolites are intended to be included within this description. Thus also to be included within the aluminosilicate zeolite definition are substantially pure silica forms of the useful zeolites described herein, that is to say those aluminosilicate zeolites having no measurable amount of aluminum (silica to alumina mole ratio of infinity) but which otherwise embody the characteristics disclosed.

Members of this particular class of zeolites, after activation, acquire an intracrystalline sorption capacity for normal hexane which is greater than that for water, i.e. they exhibit "hydrophobic" properties. This hydrophobic character can be used to advantage in some applications.

The zeolites of the particular class useful herein have an effective pore size such as to freely sorb normal hexane. In addition, their structure must provide constrained access to larger molecules. It is sometimes possible to judge from a known crystal structure whether such constrained access exists. For example, if the only pore windows in a crystal are formed by 8-membered rings, then access by molecules of larger cross-section than normal hexane is excluded and the zeolite is not of the desired type. Windows of 10-membered rings are preferred, although in some instances excessive puckering of the rings or pore blockage may render these zeolites ineffective. Twelve-membered rings usually do not offer sufficient constraint to produce the advantageous conversions, although the puckered 12-ring structure of TMA offretite shows constrained access. Other 12-ring structures may exist which may be operative.

Rather than attempt to judge from crystal structure whether or not a zeolite possesses the necessary constrained access to molecules of larger cross-section than normal paraffins, a simple determination of the "Constraint Index" as herein defined may be made by passing continuously a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 540° C. for at least 15 minutes. The zeolite is then flushed with helium and the temperature is adjusted between 290° C. and 510° C. to give an overall conversion of between 10% and 60%. The mixture of hydrocarbons is passed at 1 liquid hourly space velocity (i.e., 1 volume of liquid hydrocarbon per volume of zeolite per hour) over the zeolite with a helium dilution to give a helium to (total) hydrocarbon mole ratio of 4:1. After 20 minutes on stream, a sample of the effluent is taken and analyzed, most conveniently by gas chromatography, to determine the fraction remaining unchanged for each of the two hydrocarbons.

The "Constraint Index" is calculated as follows:

$$\text{Constraint Index} = \frac{\log_{10}(\text{fraction of hexane remaining})}{\log_{10}(\text{fraction of 3-methylpentane remaining})}$$

The Constraint Index approximates the ratio of the cracking rate constants for the two hydrocarbons. Zeolites suitable for the present invention are those having a Constraint Index of about 1 to 12. Constraint Index (CI) values for some typical materials are:

| Zeolite | C.I. |
| --- | --- |
| ZSM-5 | 8.3 |
| ZSM-11 | 8.7 |
| ZSM-12 | 2 |
| ZSM-23 | 9.1 |
| ZSM-35 | 4.5 |
| ZSM-38 | 2 |
| ZSM-48 | 3.4 |
| TMA Offretite | 3.7 |
| Clinoptilolite | 3.4 |
| Beta | 1.5 |
| H—Zeolon (mordenite) | 0.4 |
| REY | 0.4 |
| Amorphous Silica-Alumina | 0.6 |
| Erionite | 38 |

The above-described Constraint Index is an important and even critical definition of those zeolites which are useful in the instant invention. The very nature of this parameter and the recited technique by which it is determined, however, admit of the possibility that a given zeolite can be tested under somewhat different conditions and thereby exhibit different Constraint Indices. Constraint Index seems to vary somewhat with severity of operation (conversion) and the presence or absence of binders. Likewise, other variables such as crystal size of the zeolite, the presence of occluded contaminants, etc., may affect the constraint index. Therefore, it will be appreciated that it may be possible to so select test conditions as to establish more than one value in the range of 1 to 12 for the Constraint Index of a particular zeolite. Such a zeolite exhibits the constrained access as herein defined and is to be regarded as having a Constraint Index in the range of 1 to 12. Also contemplated herein as having a Constraint Index in the range of 1 to 12 and therefore within the scope of the defined class of zeolites are those zeolites which, when tested under two or more sets of conditions within the above-specified ranges of temperature and conversion, produce a value of the Constraint Index slightly less than 1, e.g. 0.9, or somewhat greater than 12, e.g. 14 or 15, with at least one other value within the range of 1 to 12. Thus, it should be understood that the Constraint Index value as used herein is an inclusive rather than a exclusive value. That is, a crystalline zeolite when identified by any combination of conditions within the testing definition set forth herein as having a Constraint Index in the range of 1 to 12 is intended to be included in the instant zeolite definition whether or not the same identical zeolite, when tested under other of the defined conditions, may give a Constraint Index value outside of the range of 1 to 12.

The particular class of zeolites defined herein is exemplified by ZSM-5, ZSM-11, ZSM-12, ZSM-23, ZSM-35, ZSM-38, ZSM-48 and other similar materials.

ZSM-5 is described in greater detail in U.S. Pat. Nos. 3,702,886 and Re. 29,948. The descriptions contained within those patents include the X-ray diffraction pattern of therein disclosed ZSM-5.

ZSM-11 is described in U.S. Pat. No. 3,709,979. The description in that patent includes the X-ray diffraction pattern of said ZSM-11.

ZSM-12 is described in U.S. Pat. No. 3,832,449. The description in that patent includes the X-ray diffraction pattern for ZSM-12.

ZSM-23 is described in U.S. Pat. No. 4,076,842 along with a specification of the X-ray diffraction pattern of the disclosed ZSM-23 zeolite.

ZSM-35 is described in U.S. Pat. No. 4,016,245 along with a description of the X-ray diffraction pattern of the zeolite.

ZSM-38 is more particularly described in U.S. Pat. No. 4,046,859. The description of that zeolite in that patent includes the X-ray diffraction pattern of ZSM-38.

ZSM-48 is more particularly described in U.S. Pat. No. 4,375,573. Such a description includes the X-ray diffraction pattern for ZSM-48.

It is to be understood that by incorporating by reference the foregoing patent documents to describe examples of specific members of the specified zeolite class with greater particularity, it is intended that identification of the therein disclosed crystalline zeolites be resolved on the basis of their respective X-ray diffraction patterns. As discussed above, the present invention contemplates utilization of aluminosilicate zeolites wherein the mole ratio of silica to alumina is essentially unbounded. The incorporation of the identified patent documents should therefore not be construed as limiting the disclosed crystalline zeolites to those having the specific compositions, e.g. silica-alumina mole ratios discussed therein, it now being known that such aluminosilicate zeolites may be substantially aluminum-free and yet, having the same crystal structure as the disclosed materials, may be useful or even preferred in some applications. It is the crystal structure, as identified by the X-ray diffraction "fingerprint", which establishes the identity of the specific crystalline zeolite material.

The specific zeolites described, when prepared in the presence of organic cations, are substantially catalytically inactive, possibly because the intra-crystalline free space is occupied by organic cations from the forming solution. They may be activated by heating in an inert atmosphere at 540° C. for one hour, for example, followed by base exchange with ammonium salts followed by calcination at 540° C. in air. The presence of organic cations in the forming solution may not be absolutely essential to the formation of this type zeolite; however, the presence of these cations does appear to favor the formation of this special class of zeolite. More generally, it is desirable to activate this type catalyst by base exchange with ammonium salts followed by calcination in air at about 540° C. for from about 15 minutes to about 24 hours.

Natural zeolites may sometimes be converted to zeolite structures of the class herein identified by various activation procedures and other treatments such as base exchange, steaming, alumina extraction and calcination, alone or in combinations. Natural minerals which may be so treated include ferrierite, brewsterite, stilbite, dachiardite, epistilbite, heulandite, and clinoptilolite.

In a preferred aspect of this invention, the zeolites hereof are selected as those providing among other things a crystal framework density, in the dry hydrogen form, of not less than about 1.6 grams per cubic centimeter. It has been found that zeolites which satisfy all three of the discussed criteria are most desired.

The dry density for known aluminosilicate zeolites may be calculated from the number of silicon plus aluminum atoms per 1000 cubic Angstroms, as given, e.g. on Page 19 of the article Zeolite Structure by W. M. Meier. This paper, the entire contents of which are incorporated herein by reference, is included in Proceedings of the Conference on Molecular Sieves, (London, April 1967) published by the Society of Chemical Industry, London, 1968.

When the crystal structure is unknown, the crystal framework density may be determined by classical pycnometer techniques. For example, it may be determined by immersing the dry hydrogen form of the zeolite in an organic solvent which is not sorbed by the crystal. Or, the crystal density may be determined by mercury porosimetry, since mercury will fill the interstices between crystals but will not penetrate the intracrystalline free space.

It is possible that the unusual sustained activity and stability of this special class of zeolites is associated with its high crystal anionic framework density of not less than about 1.6 grams per cubic centimeter. This high density must necessarily be associated with a relatively small amount of free space within the crystal, which might be expected to result in more stable structures. This free space, however, is important as the locus of catalytic activity.

Crystal framework densities of some typical zeolites, including some which are not within the purview of this invention, are:

|  | Void Volume | Framework Density |
| --- | --- | --- |
| Ferrierite | 0.28 cc/cc | 1.76 g/cc |
| Mordenite | .28 | 1.7 |
| ZSM-5, -11 | .29 | 1.79 |
| ZSM-12 | — | 1.8 |
| ZSM-23 | — | 2.0 |
| Dachiardite | .32 | 1.72 |
| L | .32 | 1.61 |
| Clinoptilolite | .34 | 1.71 |
| Laumontite | .34 | 1.77 |
| ZSM-4 (Omega) | .38 | 1.65 |
| Heulandite | .39 | 1.69 |
| P | .41 | 1.57 |
| Offretite | .40 | 1.55 |
| Levynite | .40 | 1.54 |
| Erionite | .35 | 1.51 |
| Gmelinite | .44 | 1.46 |
| Chabazite | .47 | 1.45 |
| A | .5 | 1.3 |
| Y | .48 | 1.27 |

When synthesized in the alkali metal form, the zeolite is conveniently converted to the hydrogen form, generally by intermediate formation of the ammonium form as a result of ammonium ion exchange and calcination of the ammonium form to yield the hydrogen form. In addition to the hydrogen form, other forms of the zeolite can be employed. Such other forms of the zeolite are those wherein the original alkali metal content has been reduced to less than about 50 percent by weight of the original alkali metal contained in the zeolite as synthesized, usually 0.5 percent by weight or less. Thus, the original alkali metal of the zeolite may be replaced by ion exchange with other suitable metal cations of Groups I through VIII of the Periodic Table, including, by way of example, nickel, copper, zinc, palladium, calcium or rare earth metals.

In practicing conversion processes using the catalyst of the present invention, it may be useful to incorporate the above-described crystalline zeolites with a matrix comprising another material resistant to the temperature and other conditions employed in such processes. Such matrix materials include synthetic or naturally occurring substances as well as inorganic materials such as clay, silica and/or metal oxides. The latter may be either naturally occurring or in the form of gelatinous precipitates or gels including mixtures of silica and metal oxides. Naturally occurring clays which can be composited with the zeolite include those of the montmorillonite and kaolin families, which families include the sub-bentonites and the kaolins commonly known as Dixie, McNamee-Georgia and Florida clays or others in which the main mineral constitutent is halloysite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, and silica-titania, as well as ternary compositions, such as silica-alumina-thoria, silica-alumina-zirconia, silica-alumina-magnesia and silica-magnesia-zirconia. The matrix may be in the form of a cogel. The relative proportions of zeolite component and inorganic oxide gel matrix, on an anhydrous basis, may vary widely with the zeolite content ranging from between about 1 to about 99 percent by weight and more usually in the range of about 5 to about 80 percent by weight of the dry composite.

An additional component of the conversion catalysts in accordance with the present invention comprises a minor proportion, e.g. from about 0.05% to 50% by weight of the catalyst composite, of an oxide of the metals of Groups IIIA, IVA or VA of the Periodic Chart of the Elements (Fisher Scientific Company, Catalog No. 5-702-10)

Oxides of Group IIIA, IVA and VA elements may be incorporated into the catalysts used in accordance with the present invention by processes described in the aforementioned U.S. Pat. Nos. 4,302,620, 4,302,621 and 4,302,622. The amount of these Group IIIA, IVA and VA oxides incorporated into the catalyst may be an amount sufficient to increase the yield of aromatics, e.g. BTX, relative to the amount of such aromatics which would have been produced if these oxides had been omitted from the catalysts. It will be understood that BTX denotes benzene, toluene, xylene, ethylbenzene and mixtures thereof.

The above crystalline zeolites employed may be, in accordance with the present invention, contacted with a solution of one or more compounds of the elements of Group IIIA, IVA, and VA of the Periodic Chart of the Elements. The Periodic Chart referred to herein is that version officially approved by the United States National Bureau of Standards (NBS) and the International Union of Pure and Applied Chemists (IUPAC).

Solutions of such compounds may be in any suitable solvent which is inert with respect to the metal-containing compound and the zeolite. Non-limiting examples of some suitable solvents include water, aliphatic and aromatic hydrocarbons, alcohols, organic acids (such as acetic acid, formic acid, propionic acid and so forth), and inorganic acids (such as hydrochloric acid, sulfuric acid and nitric acid). Other commonly available solvents such as halogenated hydrocarbons, ketones, ethers, etc. may be useful to dissolve some metal compounds or complexes. Generally, the most useful solvents will be found to be water and alcohol. However, the solvent of choice for any particular compound will, of course, be determined by the nature of that compound and for that reason the foregoing list should not be considered exhaustive of all of the suitable possibilities.

Representative titanium-containing compounds include titanium bromides, titanium chlorides, titanium fluorides, titanium iodides, titanium oxalate, titanium oxides, titanium sulfate, titanium sulfides, titanium sulfate, basic, titanium ethoxide, titanium propoxides, titanium butoxides, titanium methoxide, titanium nonylate and titanium stearylate. This listing is not to be taken as encompassing all of the utilizable titanium-containing compounds. It is merely intended to be illustrative of some of the representative metal compounds which those in the art will find useful in practicing the disclosed invention. The knowledgeable reader will readily appreciate that there are numerous other known titanium salts and complexes which would prove useful herein to provide solutions containing titanium suitable for combination with the zeolite in the manner hereinafter described.

Reaction of the zeolite with the treating titanium compound is effected by contacting the zeolite with such compound. Where the treating compound is a liquid, such compound can be in solution in a solvent at the time contact with the zeolite is effected. Any solvent relatively inert with respect to the treating titanium compound and the zeolite may be employed. Suitable solvents include water and aliphatic, aromatic or alcoholic liquid. The treating compound may also be used without a solvent, i.e. may be used as a neat liquid. Where the treating compound is in the gaseous phase, it can be used by itself or in admixture with a gaseous diluent relatively inert to the treating compound and the zeolite (such as helium or nitrogen) or with an organic solvent such as octane or toluene. Heating of the titanium compound impregnated catalyst subsequent to preparation and prior to use is preferred, and such heating can, if desired, be carried out in the presence of oxygen for example, in air. Although heating may be carried out at a temperature of about 150° C., higher temperatures, e.g. up to about 500° C., are preferred. Heating is generally carried out for 1-5 hours but may be extended to 24 hours or longer. While heating temperatures above about 500° C. may be employed, they are generally not necessary, and at temperatures of about 1000° C. the crystal structure of the zeolite tends to deteriorate. After heating in air at elevated temperatures, and without being limited by any theoretical considerations, it is contemplated that the titanium is actually present in the zeolite in an oxidized state, such as $TiO_2$.

The amount of titanium dioxide incorporated in the zeolite may be at least about 0.5 percent by weight. However, it is preferred that the amount of titanium dioxide in the zeolite be at least about 1.0 percent by weight, particularly when the zeolite is combined with a binder, e.g. 35 weight percent of alumina. The amount of titanium dioxide can be as high as about 30 percent by weight or more depending on the amount and type of binder present. Preferably, the amount of oxidized titanium added to the zeolite will be between about 1 and about 30 percent by weight.

The amount of titanium incorporated with the zeolite by reaction with elemental titanium or titanium-containing compound will depend upon several factors. One of these is the reaction time, i.e., the time that the zeolite and the titanium-containing source are maintained in contact with each other. With greater reaction times, all other factors being equal, a greater amount of metal is incorporated with the zeolite. Other factors upon which the amount of titanium incorporated with the zeolite is dependent include reaction temperature, concentration of the treating compound in the reaction mixture, the degree to which the zeolite has been dried prior to reaction with the metal-containing compound, the conditions of drying of the zeolite after reaction with the treating compound, and the amount and type of binder incorporated with the zeolite.

Oxides of zirconium are also effective modifying components. Examples of representative zirconium-containing compounds suitable for deposition of that metal on the zeolite include zirconium oxide, zirconium sulfate, zirconium sulfide, zirconium bromide, zirconium chloride, zirconium fluoride, zirconium nitrate, zirconium propoxides, zirconyl nitrate, zirconyl chloride, and zirconyl sulfate. As discussed above with respect to the illustrative listing of titanium compounds, the foregoing is not to be considered an exhaustive list of the utilizable zirconium salts and complexes. There are numerous zirconium compounds which the foregoing will suggest to those skilled in the art as being suitable for providing the zirconium-containing solutions for treatment of the zeolites as hereinafter described.

Reaction of the zeolite with the zirconium compounds is accomplished in substantially the same way as that recited above with respect to the titanium-containing compounds. Without being limited by any theoretical considerations, it is contemplated that the zirconium is likewise in an oxidized state, such as $ZrO_2$.

The amount of zirconium oxide incorporated in the zeolite may be at least about 0.5 percent by weight. However, it is preferred that the amount of modifier employed be at least about 1.0 percent by weight, particularly when the zeolite is combined with a binder, e.g. 35 weight percent of alumina. The amount of zirconium oxide can be as high as about 45 percent by weight or more depending on the amount and type of binder present. Preferably, the amount of oxide added to the zeolite will be between about 1 and about 40 percent by weight.

Oxides of hafnium may also be employed as a modifying component. The hafnium oxide is contemplated as being present as $HfO_2$ alone or in combination with other compounds of hafnium in an oxidized state. In all instances, regardless of the particular state of oxidation of the hafnium, its content with respect to the zeolite is computed as if it were present as $HfO_2$. Generally, the amount of $HfO_2$ in the composite catalyst will be between about 0.5 and about 50 weight percent, and preferably between about 1 and about 45 weight percent, based on the weight of the composite. Reaction of the zeolite with the hafnium-containing compound is carried out as described above with respect to the treatment with compounds of the element titanium. Examples of hafnium compounds which may be utilized include hafnium bromide, hafnium chloride, hafnium fluoride, hafnium iodide, hafnium sulfide, hafnium oxychloride and hafnium oxide. Again, this listing is not intended to be exhaustive, but rather suggestive to those of skill in the art as to the kinds of metal-containing compounds useful for treating the zeolites as herein described.

Representative vanadium-containing compounds include vanadium bromide, vanadium chloride, vanadium fluoride, vanadium iodide, vanadium oxide, vanadium oxybromide, vanadium oxychloride, vanadium oxyfluoride, vanadium sulfate, vanadium sulfide, vanadyl sulfate, vanadium hydride, vanadium tripropoxide and vanadium triethoxide. This listing is not to be taken as encompassing all of the utilizable vanadium-containing compounds. It is merely intended to be illustrative of some of the representative metal compounds which those in the art will find useful in practicing the disclosed invention. The knowledgeable reader will readily appreciate that there are numerous other known vanadium salts and complexes which would prove useful herein to provide solutions containinq vanadium suitable for combination with the zeolite in the manner hereinafter described.

The amount of vanadium pentoxide incorporated in the zeolite may be at least about 0.25 percent by weight. However, it is preferred that the amount utilized be at least about 1.0 percent by weight, particularly when the zeolite is combined with a binder, e.g. 35 weight percent of alumina. The amount of vanadium pentoxide can be as high as about 35 percent by weight or more depending on the amount and type of binder present. Preferably, the amount of vanadium pentoxide added to the zeolite will be between about 1 and about 30 percent by weight.

The amount of vanadium incorporated with the zeolite by reaction with elemental vanadium or vanadium-containing compound will depend upon several factors. One of these is the reaction time, i.e., the time that the zeolite and the vanadium-containing source are maintained in contact with each other. With greater reaction times, all other factors being equal, a greater amount of metal is incorporated with the zeolite. Other factors upon which the amount of vanadium incorporated with the zeolite is dependent include reaction temperature, concentration of the treating compound in the reaction mixture, the degree to which the zeolite has been dried prior to reaction with the metal-containing compound, the conditions of drying of the zeolite after reaction with the treating compound, and the amount and type of binder incorporated with the zeolite.

Oxides of niobium are also effective modifying components. Examples of representative niobium-containing compounds suitable for deposition of that metal on the zeolite include niobium bromide, niobium chloride, nobium fluoride, niobium oxalate, niobium oxide, niobium oxybromide, niobium oxychloride, niobium iodide, niobium ethoxide, niobium phenoxide, niobium hydride and niobium sulfide. As discussed above with respect to the illustrative listing of vanadium compounds, the foregoing is not to be considered as an exhaustive list of the utilizable niobium salts and complexes. There are numerous niobium compounds which the foregoing will suggest to those skilled in the art as being suitable for providing the niobium-containing solutions for treatment of the zeolites as hereinafter described.

The amount of niobium pentoxide incorporated in the zeolite may be at least about 0.25 percent by weight. However, it is preferred that the amount utilized comprise at least about 1 percent by weight, particularly when the zeolite is combined with a binder, e.g. 35 weight percent of alumina. The amount of niobium pentoxide can be as high as about 40 percent by weight or more depending on the amount and type of binder present. Preferably, the amount of niobium pentoxide added to the zeolite will be between about 1 and about 35 percent by weight.

Oxides of tantalum may also be employed as a modifying component. The oxidized tantalum is contemplated as being present as $Ta_2O_5$ alone or in combination with other compounds of tantalum in an oxidized state. In all instances, regardless of the particular state of oxidation of the tantalum, its content with respect to the zeolite is computed as if it were present as $Ta_2O_5$. Generally, the amount of $Ta_2O_5$ in the composite catalyst will be between about 0.25 and about 50 weight percent, and preferably between about 1 and about 40 weight percent, based on the weight of the composite. Reaction of the zeolite with the tantalum-containing compound is carried out as described above with respect to the treatment with compounds of the element titanium. Examples of tantalum compounds which may be utilized include tantalum bromide, tantalum chloride, tantalum fluoride, tantalum oxide, tantalum sulfide, tantalum oxychloride, tantalum ethoxide and tantalum hydride. Again, this listing is not intended to be exhaustive, but rather suggestive to those of skill in the art as to the kinds of metal-containing compounds useful for treating the zeolites as herein described.

Representative scandium-containing compounds include scandium acetylacetonate, scandium bromide, scandium chloride, scandium nitrate, scandium oxalate, scandium hydroxide, scandium oxide, scandium sulfate and scandium fluoride. This listing is not to be taken as encompassing all of the utilizable scandium-containing compounds. It is merely intended to be illustrative of some of the representative metal compounds which those in the art will find useful in practicing the disclosed invention. The knowledgeable reader will readily appreciate that there are numerous other known scandium salts and complexes which would prove useful herein to provide solutions containing scandium suitable for combination with the zeolite in the manner hereinafter described.

The amount of scandium oxide incorporated in the zeolite may be at least about 0.5 percent by weight. However, it is preferred that the amount utilized be at least about 1.0 percent by weight, particularly when the zeolite is combined with a binder, e.g. 35 weight percent of alumina. The amount of scandium oxide can be as high as about 30 percent by weight or more, depending on the amount and type of binder present. Preferably, the amount of scandium oxide added to the zeolite will be between about 1 and about 30 percent by weight.

The amount of scandium incorporated with the zeolite by reaction with elemental scandium or scandium-containing compound will depend upon several factors. One of these is the reaction time, i.e , the time that the zeolite and the scandium-containing source are maintained in contact with each other. With greater reaction times, all other factors being equal, a greater amount of metal is incorporated with the zeolite. Other factors upon which the amount of scandium incorporated with the zeolite is dependent include reaction temperature, concentration of the treating compound in the reaction mixture, the degree to which the zeolite has been dried prior to reaction with the metal-containing compound, the conditions of drying of the zeolite after reaction with the treating compound, and the amount and type of binder incorporated with the zeolite.

Oxides of yttrium are also effective modifying components. Examples of representative yttrium-containing compounds suitable for deposition of that metal on the zeolite include yttrium acetate, yttrium bromide, yttrium bromate, yttrium carbonate, yttrium chloride, yttrium fluoride, yttrium nitrate, yttrium oxalate, yttrium oxide, yttrium sulfate and yttrium sulfide. As discussed above with respect to the illustrative listing of scandium compounds, the foregoing is not to be considered as an exhaustive list of the utilizable yttrium salts and complexes. There are numerous yttrium compounds which the foregoing will suggest to those skilled in the art as being suitable for providing the yttrium-containing solutions for treatment of the zeolites as hereinafter described.

The amount of yttrium oxide incorporated in the zeolite may be at least about 0.5 percent by weight. However, it is preferred that the amount utilized be at least about 1.0 percent by weight, particularly when the zeolite is combined with a binder, e.g. 35 weight percent of alumina. The amount of yttrium oxide can be as high as about 40 percent by weight or more depending on the amount and type of binder present. Preferably, the amount of yttrium oxide added to the zeolite will be between about 1 and about 40 percent by weight.

Oxides of the Rare Earth elements may also be employed as the modifying component. Compounds containing RE elements will generally be of similar nature to those of scandium and yttrium recited above. For purposes of illustration, the element samarium is employed hereinafter as representative of the Rare Earth elements. The samarium oxide is contemplated as being present as $Sm_2I_3$ alone or in combination with other compounds of samarium in an oxidized state. In all instances, regardless of the particular state of oxidation of the samarium, its content with respect to the zeolite is computed as if it were present as $Sm_2O_3$. Generally, the amount of $Sm_2O_3$ in the composite catalyst will be between about 0.5 and about 50 weight percent, and preferably between about 1 and about 45 weight percent, based on the weight of the composite. Reaction of the zeolite with the samarium-containing compound is carried out as described above with respect to the treatment with compounds of the element scandium. Examples of samarium compounds which may be utilized include samarium acetate, samarium acetylacetonate, samarium bromate, samarium bromide, samarium chlorides, samarium fluorides, samarium iodides, samarium oxalate, samarium nitrate, samarium sulfate, samarium sulfide and samarium oxide. Again, this listing is not intended to be exhaustive, but rather suggestive to those of skill in the art as to the kinds of metal-containing compounds useful for treating the zeolites as herein described.

In some instances, it may be desirable to modify the crystalline zeolites by combining therewith two or more of the specified metal oxides. When such modification technique is employed, the respective oxides may be deposited on the zeolite either sequentially or from a solution containing suitable compounds of the elements, the oxides of which are to be combined with the zeolite. The amounts of oxides present in such instance are in the same range as specified above for the individual oxides, with the overall added oxide content being between about 1 and about 45 weight percent of the composite.

The aromatization conditions suitable for use in accordance with the present invention may include, e.g. a temperature of from about 200° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20.

The feedstock to be aromatized may comprise one or more $C_2$-$C_{12}$ alkanes, e.g. $C_5$-$C_8$ alkanes, especially straight chain alkanes. A suitable feedstock may be a petroleum refinery stream having a boiling point at atmospheric pressure of less than about 300° F (i.e., about 149° C.), e.g. a gasoline stream from an atmospheric distillation column derived from a paraffinic crude.

In the Examples and Comparative Example which follow all aromatics conversion reactions were conducted at atmospheric pressure.

COMPARATIVE EXAMPLE

For a reference run n-octane was converted over unmodified HZSM-5 at WHSV=1.0 at various temperatures. The results are listed below. Conversion of n-octane was almost complete at all temperatures studied.

| Temperature °C. | 400 | 500 | 550 |
|---|---|---|---|
| % Selectives | | | |
| C1-C7 aliphatics | 78 | 79 | 63 |
| BTX | 15.6 | 18.0 | 34.3 |
| C9+ aromatics | 4.0 | 2.6 | 2.1 |
| Total aromatics | 19.6 | 20.6 | 36.4 |

EXAMPLE 1

A scandium modified ZSM-5 catalyst (i.e., ScZSM-5), essentially equivalent to the HZSM-5 catalyst of the Comparative Example, except that the ScZSM-5 catalyst contained 4.57 weight percent Sc in the form of an oxide, was prepared in the following manner.

To a solution of 4.0 g of scandium nitrate in 3 ml of water maintained at ambient temperature was added 1.5 g of HZSM-5 ($SiO_2/Al_2O_3=70$). The mixture was maintained at room temperature for 24 hours. After filtration and drying at about 80° C. for 2 hours, the residue was calcined at 500° C. for an additional 3 hours to yield 1.85 g of Sc=ZSM-5. The content of scandium was found on analysis to be 11.8 weight percent.

n-Octane reaction was run over this ScZSM-5 catalyst at 500° C. at WHSV=1.0. The conversion was nearly complete. The BTX yield was 26.5% and total aromatics were 29.0%, a considerable improvement over the unmodified HZSM-5 of the Comparative Example.

EXAMPLE 2

A titanium modified ZSM-5 catalyst (i.e. TiZSM-5), essentially equivalent to the HZSM-5 catalyst of the Comparative Example, except that the TiZSM-5 catalyst contained 11.4 weight percent Ti in the form of an oxide, was prepared in the following manner.

[Preparation of Ti-modified zeolite]

Mixed 1.5 g HZSM-5 ($SiO_2/Al_2O_3=70$) with 5 ml of titanium butoxide at 60° to 70° C. and maintained the mixture at that temperature for 18 hours. After filtration and drying at 80° C. for 3 hours, the zeolite was calcined for 2.5 hours more at 500° C. Recovered 1.71 g of Ti-ZSM-5. The process was repeated with 1.5 g of the recovered Ti-ZSM-5 at ambient temperature to yield 1.9 g of modified catalyst. The content of titanium was found to be 18.9 percent by weight.

Conversion of n-octane was run the same way as in Example 1 except the TiZSM-5 catalyst was used. The conversion was almost 100%. The BTX yield was 25.1% and the total aromatics were 27.3%.

EXAMPLE 3

A vanadium modified ZSM-5 catalyst (i.e. VZSM-5), essentially equivalent to the HZSM-5 catalyst of the Comparative Example, except that the VZSM-5 catalyst contained 6.47 weight percent V in the form of an oxide, was prepared in the following manner. To a solution of 1.5 g vanadium trichloride in 5 ml of ethanol at 50° C. was added 1.5 g HZSM-5 ($SiO_2/Al_2O_3=70$). The mixture was maintained at about 60° C. for 22 hours. After filtration and drying at about 80° C. for 1.5 hours, the residue was calcined at 500° C. for 2.5 hours more to give 1.68 g of V-ZSM-5.

To the filtrate of the above $VCl_3$/EtOH solution was added 1.5 g of V-ZSM-5 (prepared above) at 60° C. and the mixture was maintained at 60° C. for 22 hours. After the same work-up procedure 1.52 g V-ZSM-5 were obtained. The content of vanadium was found to be 8.80 percent by weight.

Conversion of n-octane was run with this VZSM-5 at WHSV=1. At 500° C., the conversion was 100% and BTX was 30.4% and the total aromatics were 32.1%. At 550° C., the conversion was 100% and BTX yield was 37.6% and the total aromatics 39.2%. Both runs showed considerable improvement over the HZSM-5 runs of the Comparative Example.

What is claimed is:

1. A process for producing aromatic hydrocarbons, said process comprising contacting one or more $C_2$-$C_{12}$ alkanes with a catalyst comprising a crystalline zeolite material having the structure of ZSM-5 or ZSM-11, said contacting taking place under aromatization conditions including a temperature of from about 200° C. to about 700° C., a pressure of from about 0.1 atmosphere to about 60 atmospheres, a weight hourly spaced velocity (WHSV) of from about 0.1 to about 400 and a hydrogen/hydrocarbon mole ratio of from about 0 to about 20, said catalyst further comprising an oxide of a Group IIIA, IVA or VA element, said oxide being incorporated into said catalyst by a modification process comprising the steps of:
   (i) contacting said ZSM-5 or ZSM-11 with a solution or neat liquid of a compound of said Group IIIA, IVA or VA element, thereby impregnating said ZSM-5 or ZSM-11 with said compound; and
   (ii) heating said impregnated ZSM-5 or ZSM-11 or step (i) for at least one hour at a temperature of at least 150° C.

2. A process according to claim 1, wherein said Group IIIA, IVA or VA element is selected from the group consisting of Sc, Ti and V.

3. A process according to claim 1, wherein said zeolite material is an aluminosilicate zeolite having a silica/alumina mole ratio of at least 12.

4. A process according to claim 3, wherein said zeolite material has the structure of ZSM-5.

5. A process according to claim 1 wherein said catalyst further comprises a binder.

6. A process according to claim 1, wherein said oxide is present in said catalyst in an amount sufficient to increase the yield of aromatics relative to the amount of such aromatics which would have been produced if said oxide had been omitted from said catalyst.

7. A process according to claim 1, wherein said oxide is present in said catalyst in an amount sufficient to increase the yield of BTX relative to the amount of such BTX which would have been produced if said oxide had been omitted from said catalyst.

8. A process according to claim 1, wherein said element is a Group IIIA or IVA element and said element is present in said catalyst in an amount of at least 0.5 weight percent.

9. A process according to claim 1, wherein said element is a Group VA element and said element is present in said catalyst in an amount of at least 0.25 weight percent.

10. A process according to claim 1, wherein said element is present in said catalyst in an amount of between 1 and 30 weight percent.

11. A process according to claim 1, wherein $C_5$–$C_8$ straight chain alkanes are converted into aromatic hydrocarbons.

12. A process for producing BTX, said process comprising contacting one or more $C_5$–$C_8$ straight chain alkanes with a catalyst comprising an aluminosilicate ZSM-5 having a silica/alumina mole ratio of at least 12, said contacting taking place under aromatization conditions including a temperature of from about 200° C. to about 700° C., a pressure of from about 0.1 atmosphere to about 60 atmospheres, a weight hourly space velocity (WHSV) of from about 0.1 to about 400 and a hydrogen/hydrocarbon mole ratio of from about 0 to about 20, said catalyst further comprising at least 1 percent by weight of an oxide of a Group IIIA, IVA or VA element, said oxide being incorporated into said catalyst by a modification process comprising the steps of:

(i) contacting said ZSM-5 or ZSM-11 with a solution or neat liquid of a compound of said Group IIIA, IVA or VA element, thereby impregnating said ZSM-5 or ZSM-11 with said compound; and (ii) heating said impregnated ZSM-5 or ZSM-11 of step (i) for at least one hour at a temperature of at least 150° C.

13. A process according to claim 1, wherein said Group IIIA, IVA or VA metal is selected from the group consisting of Sc, Ti and V.

* * * * *